(12) United States Patent
Mehta et al.

(10) Patent No.: US 10,376,271 B2
(45) Date of Patent: Aug. 13, 2019

(54) ARTHROSCOPIC TUNNEL GUIDE FOR ROTATOR CUFF REPAIR

(71) Applicant: Vishal Mahul Mehta, Naperville, IL (US)

(72) Inventors: Vishal Mahul Mehta, Naperville, IL (US); Brian L. Lipford, Bel Air, MD (US); Eric Schneider, Catonsville, MD (US); Ben Lane, Hydes, MD (US)

(73) Assignee: Vishal Mahul Mehta, Naperville, IL (US)

( * ) Notice: Subject to any disclaimer, the term of this patent is extended or adjusted under 35 U.S.C. 154(b) by 0 days.

(21) Appl. No.: 14/675,201

(22) Filed: Mar. 31, 2015

(65) Prior Publication Data

US 2015/0272600 A1 Oct. 1, 2015

Related U.S. Application Data

(63) Continuation of application No. 13/956,920, filed on Aug. 1, 2013, now Pat. No. 9,072,530, which is a continuation of application No. 12/694,356, filed on Jan. 27, 2010, now Pat. No. 8,556,911.

(60) Provisional application No. 61/231,279, filed on Aug. 4, 2009, provisional application No. 61/147,565, filed on Jan. 27, 2009.

(51) Int. Cl.
*A61B 17/16* (2006.01)
*A61B 17/17* (2006.01)

(52) U.S. Cl.
CPC ...... *A61B 17/1764* (2013.01); *A61B 17/1631* (2013.01); *A61B 17/1642* (2013.01); *A61B 17/1684* (2013.01); *A61B 17/17* (2013.01); *A61B 17/1778* (2016.11)

(58) Field of Classification Search
CPC ............ A61B 17/1631; A61B 17/1615; A61B 17/1633; A61B 17/1637; A61B 17/164; A61B 17/1642
USPC ........................ 606/79–86 R, 96–98; 408/127
See application file for complete search history.

(56) References Cited

U.S. PATENT DOCUMENTS

| | | |
|---|---|---|
| 550,783 A | 12/1895 | Elliott et al. |
| 4,541,423 A | 9/1985 | Barber |
| 4,922,897 A | 5/1990 | Sapega et al. |
| 4,945,904 A | 8/1990 | Bolton et al. |
| 5,330,468 A | 7/1994 | Burkhart |
| 6,120,511 A | 9/2000 | Chan |
| 6,447,514 B1 * | 9/2002 | Stalcup ............... A61B 17/164 606/63 |
| 6,514,274 B1 | 2/2003 | Boucher et al. |
| 7,604,636 B1 * | 10/2009 | Walters ............. A61B 17/1642 606/80 |
| 2001/0002436 A1 | 5/2001 | Bowman et al. |

(Continued)

FOREIGN PATENT DOCUMENTS

| | | |
|---|---|---|
| WO | WO 2008/008522 A1 | 1/2008 |
| WO | WO2008/54085 | 2/2008 |
| WO | WO 2008/103606 A2 | 8/2008 |

*Primary Examiner* — Matthew J Lawson
(74) *Attorney, Agent, or Firm* — Benesch, Friedlander, Coplan & Aronoff LLP

(57) ABSTRACT

A drill guide assembly for drilling a tunnel having a fixed, non-zero radius of curvature, where the drill guide assembly includes a housing and a sleeve, or cutting tube, configured to reciprocate within the distal portion where the sleeve, or cutting tube, is configured to receive a bone cutting instrument.

16 Claims, 9 Drawing Sheets

(56) References Cited

U.S. PATENT DOCUMENTS

| | | | |
|---|---|---|---|
| 2003/0191474 A1* | 10/2003 | Cragg | A61B 17/1671 606/79 |
| 2004/0092933 A1 | 5/2004 | Shaolian et al. | |
| 2005/0043805 A1 | 2/2005 | Chudik | |
| 2005/0143745 A1 | 6/2005 | Hodorek et al. | |
| 2005/0257481 A1 | 11/2005 | Shaw | |
| 2008/0114365 A1* | 5/2008 | Sasing | A61B 17/1622 606/80 |
| 2010/0114098 A1* | 5/2010 | Carl | A61B 17/1642 606/80 |

\* cited by examiner

ARTHROSCOPIC TUNNEL GUIDE FOR ROTATOR CUFF REPAIR

CROSS-REFERENCE TO RELATED APPLICATIONS

This application claims the benefit of U.S. Non-Provisional application Ser. No. 13/956,920 filed Aug. 1, 2013, which is a continuation of U.S. Pat. No. 8,556,911 filed Jan. 27, 2010, which claims priority to U.S. Provisional Application No. 61/231,279 filed Aug. 4, 2009, and U.S. Provisional Application No. 61/147,565 filed Jan. 27, 2009, the entirety of which are incorporated herein by reference.

BACKGROUND

Traditional methods of tissue repair to the shoulder or other joint areas are accomplished through open surgery. For example, rotator cuff repair is a type of surgery to fix a torn tendon in the shoulder. The rotator cuff is a group of muscles and tendons which form a covering, or a "cuff," around the top of the upper arm bone, referred to as the humerus. The rotator cuff holds the humeral head in place in the shoulder joint and enables the arm to elevate and rotate.

The rotator cuff may tear through a single traumatic injury or overuse. A partial tear may require only a trimming or smoothing procedure referred to as a "debridement." A complete tear, however, may be repaired by suturing the two sides of the tendon back together. Moreover, if the tendon is torn away from a location referred to as the greater tuberosity atop the humerus, it is reattached directly back to the humerus.

One method to attach the tendon back to the humerus is accomplished through open surgery. Open surgery requires the surgeon to make a two to three-inch incision in the shoulder area. The deltoid muscle is then cut through and/or separated in order to gain access to the damaged tendon. A small trough at the top of the humerus is created and small holes are drilled therethrough. Transosseous sutures are weaved or stitched through the rotator cuff and passed through the small holes to secure the rotator cuff to the humerus. Alternatively, anchors may be used to attach the tendon to the humerus. Although an effective method of repairing detached rotator cuff tendons, open surgery is not without its consequences. Pain, swelling, increased chance of infection, and prolonged recovery times are just a few examples of the adverse effects of open surgery.

To reduce the complications associated with open surgery, another method of repairing a torn rotator cuff is preformed arthroscopically. Arthroscopic surgery has some advantages as a result of its minimally invasive nature. Thus, the risks of infection, blood loss, and the like, are lower than compared to open surgery. However, because the incisions made during arthroscopic surgery are typically six to eight millimeters wide, the instruments used to repair the rotator cuff are more limited in size.

For example, suture anchors are commonly used in arthroscopic surgery to repair the rotator cuff tears. A suture anchor is configured to be secured into the humeral head and is designed to attach a portion of the damaged or torn rotator cuff to the greater tuberosity of the humeral head. The anchor portion is embedded into the bone and has at least one suture attached thereto. The suture extends from the anchor and secures the damaged rotator cuff tendon to the greater tuberosity of the humeral head.

However, in some patients, the bone quality in the greater tuberosity may be poor, thereby inhibiting, or providing less optimal, securement of the suture anchors within the humeral head. In such situations, the chances of bone fragmentation and anchor displacement may affect the integrity of the repair.

Attempts have also been made to use the techniques of open surgery repair, arthroscopically. For example, others have attempted to accomplish arthroscopic repair of the rotator cuff tendons through the bone tunnel and suture method explained above. However, the upper limits on the size of the available instruments which may be used to form bone tunnels are restricted by the diameters of the arthroscopic portals.

BRIEF SUMMARY

In order to address the drawbacks with open surgical techniques and the arthroscopic attachment devices discussed above, an orthopedic drill guide assembly having a sleeve with a fixed radius of curvature to form a tunnel within a bone is disclosed. In one embodiment, an orthopedic drill guide assembly for drilling a tunnel in a bone includes a drill guide housing having a proximal portion, a distal portion, where the distal portion is curved in shape. A body portion is disposed between the proximal portion and the distal portion. A passage is formed within the drill guide housing and extends from the proximal portion to the distal portion such that the passage has a fixed radius of curvature within the distal portion. A sleeve having a lumen therethrough, where the sleeve has a proximal end and a distal end, is slidingly disposed within the passage of the distal portion of the drill guide housing and has a fixed radius of curvature which is substantially equal to the radius of curvature of the passage within the distal portion. The sleeve is configured to extend from the distal portion and further configured to receive a bone cutting instrument.

In another embodiment, an orthopedic drill guide assembly for drilling a tunnel in a bone includes a drill guide housing having a proximal portion and a distal portion. A body portion is disposed between the proximal portion and the distal portion and a passage is formed within the drill guide housing and extending from the proximal portion to the distal portion. A tube is slidingly disposed within the passage of the distal portion of the drill guide housing and has a lumen therethrough and having a proximal end and a distal end. The tube is made out of a shape memory alloy and can to extend from the distal portion and further configured to receive a bone cutting instrument.

A method of arthroscopically drilling a tunnel through a bone includes providing a drill guide with a drill guide housing having a distal portion, a sleeve slidingly disposed within the drill guide housing, a flexible shaft disposed within the drill guide housing and coupled with the sleeve, and a bone cutting tip coupled to at least one of the distal end of the flexible shaft and/or the sleeve. The distal portion of the drill guide housing is placed against a desired entry port location on the bone and the bone cutting tip and sleeve are advanced into the bone, where the bone cutting tip travels along a fixed non-zero radius of curvature defined by the sleeve. A tunnel is created within the bone having a fixed non-zero radius of curvature substantially equal to the fixed non-zero radius of curvature of the sleeve.

DETAILED DESCRIPTION

Figure 1:
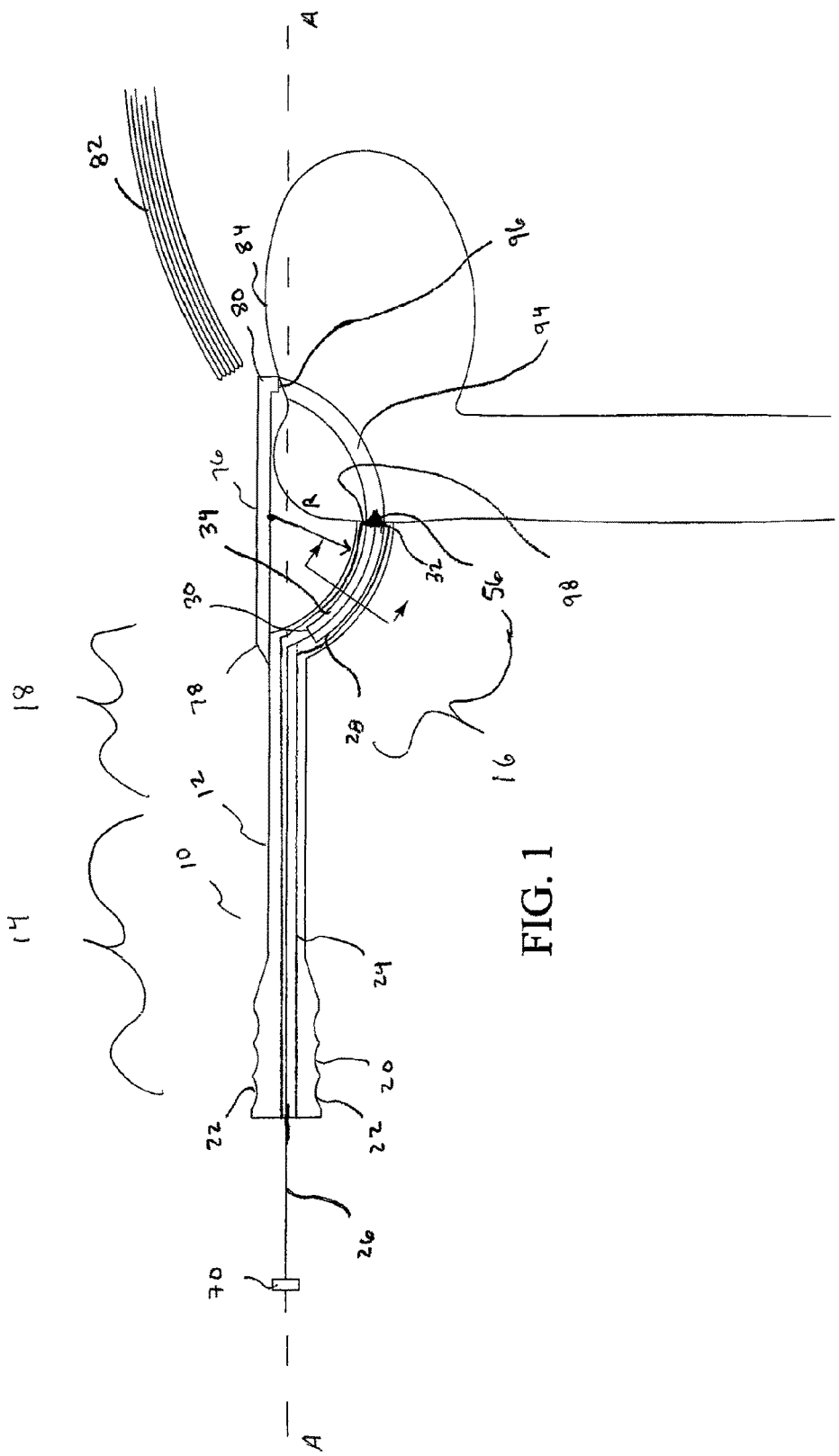
FIG. 1 is perspective view of one embodiment of the drill guide assembly.

The embodiments below are described with reference to the drawings in which like elements are referred to by like numerals. The relationship and functioning of the various elements are better understood by the following detailed description. However, the embodiments as described below are by way of example only, and the invention is not limited to the embodiments illustrated in the drawings.

Throughout this specification and in the appended claims the term "distal" with respect to such a device is intended to refer to a location, or a portion of the device, that is further away from the user of the device. The term "proximal" is intended to refer to a location, or a portion of the device, that is closer to the user of the device.

The embodiments of the orthopedic guide device described below are configured to create tunnels with a substantially fixed and constant radius of curvature within a bone, and to permit a suture, or fastening device similar thereto, to be disposed through the tunnel to secure a portion of a ligament, tendon, a bone, or other various parts of the anatomy.

In one embodiment, and as shown in FIG. 1, a drill guide assembly 10 is shown. The drill guide assembly 10 consists of a housing 12 defining an A axis. The drill guide assembly 10 comprises a proximal portion 14, a distal portion 16, and a body portion 18 disposed between the proximal 14 and distal 16 portions. The relative lengths of the proximal 14, distal 16, and body 18 portions may vary between applications, and may be dependent on the desired maneuverability and characteristics for a particular use.

In the embodiment shown in FIG. 1, the body portion 18 has a substantially linear shape, however, the shape of the body portion 18 may vary depending on the intended use of the assembly 10. For example, the body portion 18 may also have a shape having a non-zero radius of curvature, for improved ergonomics or use during operation.

A handle 20 may form a part of the proximal portion 14 for gripping the housing 12. The handle 20 may have a series of indentations 22 or have a gripping material located thereon in order to accommodate a user's hand. The handle 20 may also be located on any other portion of the housing 12. For example, the handle 20 may form a part of the body portion 18 to provide more controlled movement of the drill guide assembly 10 during use.

As further shown in FIG. 1, a passage 24 is formed within the housing 12. The passage 24 generally extends from the proximal portion 14 of the housing 12 to the distal portion 16 of the housing 12, along the A axis. The passage 24 is configured to accommodate a flexible shaft 26, such as a guide wire or the like, such that the flexible shaft 26 can rotate and/or reciprocate within the passage 24. The diameter and cross-sectional shape of the flexible shaft 26 and/or passage 24 may vary along the length of the housing 12. Moreover, the passage 24 may only extend along a portion of the housing 12 such that an entrance may be formed along any portion of the housing 12 to allow the flexible shaft 26 to enter the housing 12. The passage 24 and/or the flexible shaft 26 may be coated with a lubricating compound, such as graphite or Teflon, or be made out of a material having a low coefficient of friction to reduce the frictional force generated by the relative movement between the passage 24 and the flexible shaft 26. Such materials include metal alloys and plastics.

Figure 2:
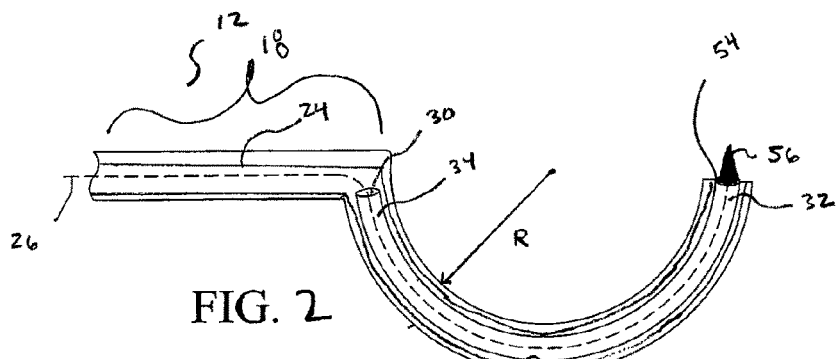
FIG. 2 is a perspective view of one embodiment of the distal end of the drill guide housing.

As shown in FIGS. 1 and 2, the distal portion 16 of the housing 12 may be curved in shape. The angular displacement and radius of curvature, R, of the distal portion 16 may vary between each embodiment and is application dependent. However, the radius of curvature for the distal portion 16 will remain substantially constant within each embodiment. The distal portion 16 may have an arc-shape ranging from 0 to 300 degrees, and the fixed non-zero radius of curvature may be 0 to 50 mm. However, the exact radius of curvature desired is dependent on the bone thickness and the intended use. For example, in the embodiment shown in FIG. 2, the distal portion 16 of the housing 12 has a semi-circular shape with a constant radius of curvature, R.

The passage 24 formed within the distal portion 16 of the housing 12 may have a shape and a radius of curvature similar to that of the distal portion 16. As shown in FIGS. 1 and 2, the passage 24 within the distal portion 16 is designed to accommodate a sleeve 28. The sleeve 28 is configured to reciprocate within, and extend from, the distal portion 16 of the housing 12. The sleeve 28 has a proximal end 30 and a distal end 32, defining a lumen 34 therethrough. The sleeve 28 may be made out of a material similar to that of the housing 12. The radius of curvature of the sleeve 28 is substantially equal to the radius of curvature of the passage 24 of the distal portion 16 of the housing 12. Although the length of the sleeve 28 may vary, its maximum length, in the embodiments of FIGS. 1 and 2, is limited to the circumferential length of the distal portion 16 and has substantially the same radius of curvature as the distal portion 16.

Figure 3:
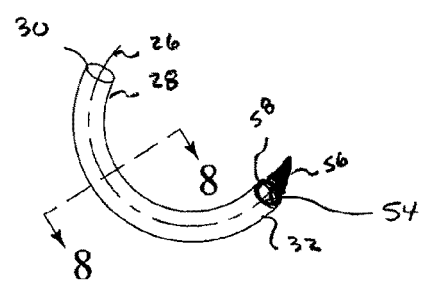
FIG. 3 is a perspective view of one embodiment of the sleeve.
Figure 4:
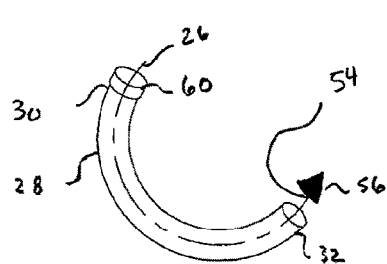
FIG. 4 is a perspective view of one embodiment of the sleeve.

The sleeve 28 is configured to accommodate a bone cutting tip 56. The bone cutting tip 56 is disposed on a distal end 54 of the flexible shaft 26. The bone cutting tip 56 is designed to create a hole, or tunnel 94, having approximately the same diameter of the bone cutting tip 56 through a medium, such as bone. As shown in FIGS. 3 and 4, the bone cutting tip 56 is fixedly coupled with the distal end 54 of the flexible shaft 26, with the bone cutting tip 56 being disposed adjacent to the distal end 32 of the sleeve 28. The bone cutting tip 56 and the flexible shaft 26 are configured to be able to rotate with respect to the sleeve 28. The bone cutting tip 56 forms a hole having a diameter which is at least equal to the outer diameter of the sleeve 28, to permit the sleeve 28 to be advanced through the hole or tunnel 94 formed within the working medium. The bone cutting tip 56 may be formed out of any suitable metal alloy or plastic.

Turning back to FIG. 1, an outer stop member 70 is located along the flexible shaft 26 at a location proximal to the proximal portion 14 of the housing 12. The outer stop member 70 is configured to abut an external surface of the proximal portion 14 of the housing 12 to limit the distance the flexible shaft 26 and/or sleeve 28 may travel within the housing 12. However, the location of the outer stop member 70 is dependent on the entrance location of the flexible shaft 26 with respect to the housing 12; and thus it is not necessary that the outer stop member 70 is positioned at a location proximal to the proximal portion 14 of the housing 12. A series of graduated markings may be positioned along the flexible shaft 26 and viewable external to the housing 12 to indicate the amount of linear or angular displacement of the bone cutting tip 56 with respect to the housing 12.

Located along the body portion 18 of the housing 12, and configured to reciprocate along, and extend from, the housing 12, there may be an exit port locator 76, as shown in FIG. 1. The exit port locator 76 has a first end 78 and a second end 80. The first end 78 of the exit port locator 76 is coupled with the body portion 18 of the housing 12, and is configured to slide along the body portion 18 from a retracted position where the second end 80 of the exit port locator 76 is adjacent to, and in contact with, the body portion 18, to a second position, where the second end 80 is fully extended from the body portion 18. In the second position, which is shown in FIG. 1, the location second end 80 of the exit port locator 76 is approximately the same location where the bone cutting tip 56 would be located when it is extended and rotated approximately 90° from the distal portion 16 of the housing 12. Accordingly, the second end 80 of the exit port locator 76, when in the second position, identifies the exit location of the tunnel 94 or aperture prior to the commencement of the drilling process. The exit port locator 76 may also be used to secure the drill guide assembly 10 during the drilling process. For ease of identification, the second end 80 may be L-shaped or have radiopaque markers to aid in locating the second end 80 during operation. The exit port locator 76 may be made out of the same material as the housing 12 or any other material which is suitable for surgical use. The exit port locator 76 may be spring loaded or have a locking mechanism to lock the exit port locator 76 when in the first and/or second position, or any position therebetween.

Figure 5:
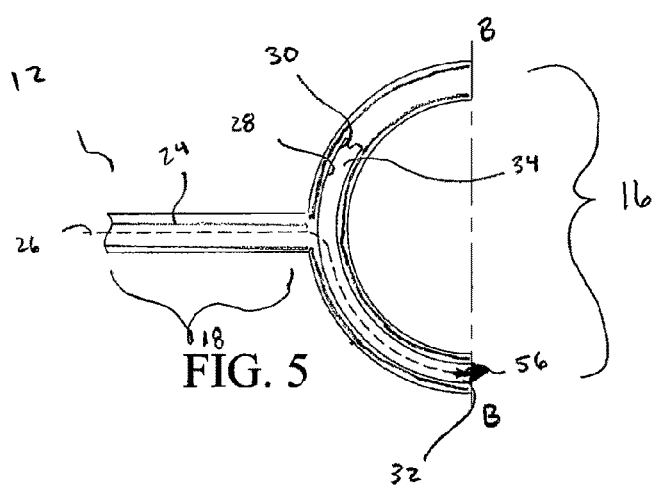
FIG. 5 is a perspective view of one embodiment of the distal end of the drill guide housing.

Turning now to FIG. 5, it can be appreciated that the orientation of the distal portion 16 may vary with respect to the housing 12. The different configurations of the distal portion 16 may cause the configuration of the exit port locator 76 to change. For example, in this embodiment, distal portion 16 has a semicircular shape defined along a vertical axis B, where the axis A of the housing 12 is substantially perpendicular to the vertical axis B. It can be appreciated that the body portion 18 of the housing 12 may be positioned in any location along the curve of the distal portion 16, depending on the intended use of the drill guide assembly 10.

Figure 7:
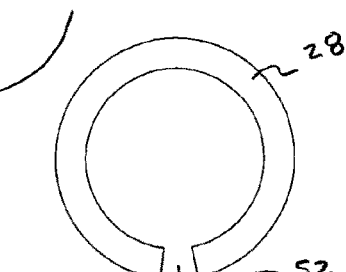
FIG. 7 is a frontal view of one embodiment of the sleeve.
Figure 6:
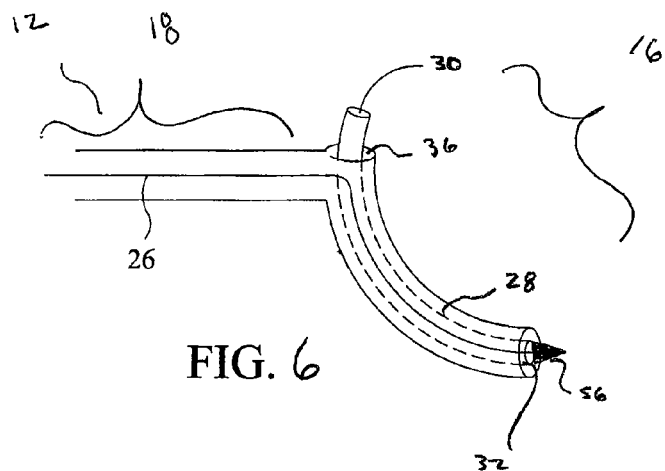
FIG. 6 is an exploded view of one embodiment of the distal end of the drill guide housing.

In an alternative embodiment, as shown in FIG. 6, the body portion 18 of the housing 12 may have an aperture 36, from which a proximal end 30 of the sleeve 28 may extend from. In this embodiment, the length of the sleeve 28 may be greater than the circumferential length of the distal portion 16. Further, as shown in the FIG. 7 embodiment, the sleeve 28 may have a channel 52 formed at least partially along the length of the sleeve 28. The diameter of the channel 52 is at least wide enough to receive the flexible shaft 26. The channel 52 permits the flexible shaft to enter the sleeve 28 at a location other than through the proximal end 30 of the sleeve 28 as was the case in the embodiment of FIG. 1. The channel 52 may be formed along a portion or the entire length of the sleeve 28. The exact width and length of the channel 52 will be dictated by the size of the flexible shaft 26 and the intended use of the drill guide assembly 10.

Figure 8:
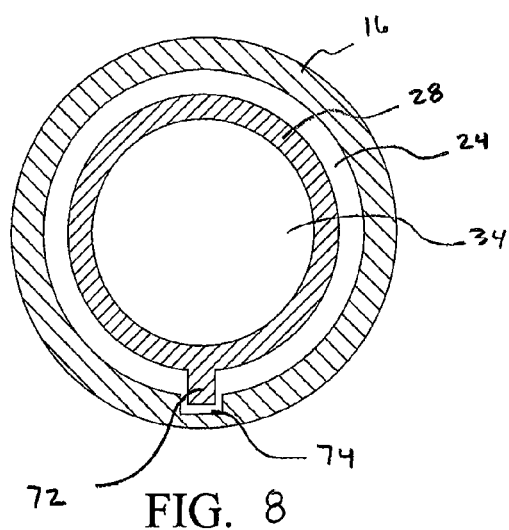
FIG. 8 is a cross-sectional view of the distal portion of the drill guide housing.

A channel and a guide configuration may prevent unwanted relative rotational movement between the sleeve 28 and the distal portion 16 of the housing 12, which could bind the sleeve 28 within the distal portion 16 during operation. For example, one configuration is shown in FIG. 8, which is a cross-sectional view of the distal portion 16 of the housing 12 and the sleeve 28 taken along the line 8-8 of FIG. 3. As shown in FIG. 8, the sleeve 28 may include a guide 72, external thereto, extending along at least a portion of the sleeve 28. A channel 74 may be formed within the distal portion 16 of the housing 12 which is aligned with, and is configured to receive, the guide 72 of the sleeve 28. The channel 74 extends at least along a portion of the distal portion 16. In operation, the guide 72 and channel 74 are configured to linearly, but not rotationally, reciprocate relative to one another. It can be appreciated that the guide 72 may extend along the distal portion 16 of the housing 12 and the channel may be formed within the sleeve 28.

Figure 9A:
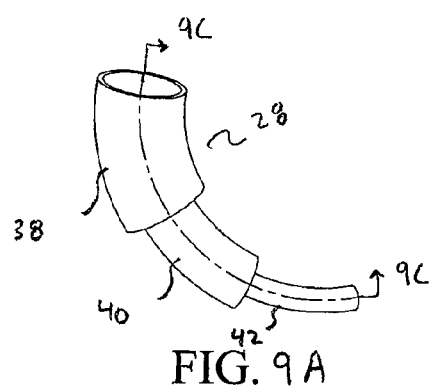
FIG. 9A is a perspective view of one embodiment of the sleeve.
Figure 9B:
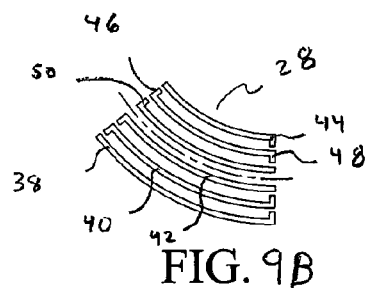
FIG. 9B is a fragmentary view of one embodiment of the sleeve.
Figure 9C:
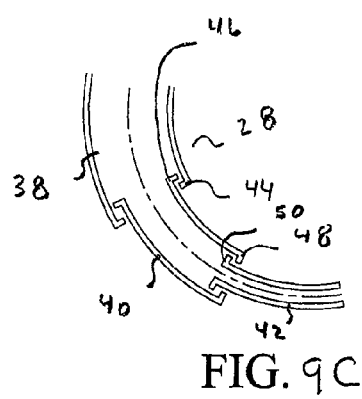
FIG. 9C is another fragmentary view of the embodiment of the sleeve shown in FIG. 9B.

In another alternative embodiment, as shown in FIGS. 9A-C, the sleeve 28 may have multiple segments with telescopic properties, such that, for example, the sleeve 28 may consist of a base portion 38, a first telescoping portion 40, and a second telescoping portion 42. This configuration may allow the sleeve 28 to adjust to different lengths. As shown in FIG. 9C, the first telescoping portion 40 is configured to telescope, or extend, from the base portion 38 in a distal direction, and the second telescoping portion 42 is configured to further telescope from the first telescoping portion 40. In alternative implementations, the distal portion 16 may also have a portion (not shown) with similar telescoping characteristics as this embodiment of the sleeve 28. It is also contemplated that both the sleeve 28 and the distal portion 16 may be configured to respectively telescope during operation within the same embodiment. The sleeve 28 and/or the distal portion 16 may be retracted into its original, or first, position upon completion of the operation.

A distal end 44 of the base portion 38 may be designed to prevent the first telescoping portion 40 from decoupling with the base portion 38. For example, FIGS. 9B and C are cross-sectional views of the sleeve 28 in a retracted position and an extended position, respectively. The distal end 44 is flanged shaped and configured to abut a proximal end 46 of the first telescoping portion 40. Using a similar configuration, a distal end 48 of the first telescoping portion 40 is configured to abut a proximal end 50 of the second telescoping portion 42, when the sleeve 28 is in a fully extended position, as shown in FIG. 9C. It can be appreciated that the number, length, and diameter of the telescoping portions may vary and are application dependent. Accordingly, the overall angular extension of the sleeve 28 can range anywhere between 0-180°.

Figure 10:
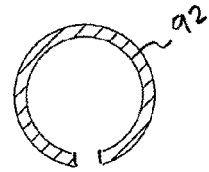
FIG. 10 is a cross-sectional view of one embodiment of the fastener.

Independent of the configuration of the sleeve 28, the bone cutting tip 56, in one embodiment, as shown in FIG. 3, is rotatably coupled with the distal end 32 of the sleeve 28 by a coupling fastener 58. The coupling fastener 58 may include a c-clip 92 as shown in FIG. 10, a rotatable coupler, or the like. The coupling fastener 58 couples the bone cutting tip 56 to the distal end 32 of the sleeve 28 but permits relative rotational movement between the bone cutting tip 56 and the sleeve 28, as the bone cutting tip 56 is advanced through the medium.

Alternatively, a stop member 60 may be located along the length of the flexible shaft 26 as shown in FIG. 4. The stop member 60 may be located at a position adjacent to the proximal end 30 of the sleeve 28, and have a diameter substantially equal to or greater than the inner diameter of the sleeve 28, but less than the diameter of the passage 24. In this embodiment, the bone cutting tip 56 is not directly coupled with the distal end 32 of the sleeve 28, but instead is free to translate with respect to the sleeve 28. However, the amount of relative axial translation between the sleeve 28 and the bone cutting tip 56 along the flexible shaft 26 is governed by the location of the stop member 60 along the flexible shaft 26. For example, if the length of the flexible shaft 26 between the stop member 60 and the bone cutting tip 56 is substantially equal to the length of the sleeve 28, minimal relative translational movement between the sleeve 28 and bone cutting tip 56 will exist. Conversely, if the length of the flexible shaft 26 between the stop member 60 and the bone cutting tip 56 is greater than the length of the sleeve 28, the bone cutting tip 56 will be permitted to have limited relative translational movement between it and the distal end 32 of the sleeve 28. The displacement of the bone cutting tip 56 with respect to the distal end 32 of the sleeve 28 will permit debris and other medium fragments from being lodged in the tunnel 94 created by the bone cutting tip 56. Instead, such debris and fragments will be displaced into the sleeve 28 and cleared away from the working area.

Figure 11:
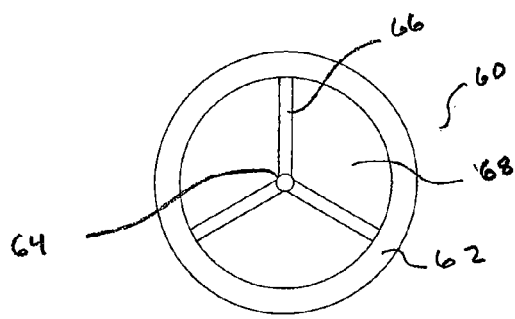
FIG. 11 is a front view of one embodiment of the stop member.

In one embodiment, the stop member 60, as shown in FIG. 11, has a outer portion 62 configured to abut the proximal end 30 of the sleeve 28 and an inner portion 64 adapted to receive the flexible shaft 26, with the outer 62 and inner 64 portions connected by a series of struts 66 which radially extend from the inner portion 64 to the outer portion 62. In this configuration, a series of apertures 68 are formed within the stop member 60, to enable debris and other fragments to pass through the stop member 60 towards the proximal portion 14 of the housing 12. It can be appreciated that the number of struts 66 and apertures 68 may vary depending on the application.

The drill guide assembly 10 is intended to be used for arthroscopic surgery. For example, the drill guide assembly 10 may be used for arthroscopic shoulder surgery, and specifically, for reattaching a torn rotator cuff tendon 82 back to a proximal end of a humerus 84, as shown in FIG. 1. The drill guide assembly 10 can be operated as a hand-held device, or alternatively, be configured to be coupled with a frame to fix the position of the drill guide assembly 10 once the entry port location is identified.

During the surgical procedure, a surgeon investigates the glenohumeral joint by creating a posterior arthroscopic portal. An arthroscope (not shown) is introduced into the glenohumeral joint to an area proximate to the damaged rotator cuff tendon. An anterior portal having a diameter of 6 to 8 mm is made and an anterior cannula is inserted into the portal to perform a standard glenohumeral arthroscopy procedure. Once the damaged area is identified, the arthroscope and anterior cannula are re-positioned to the subacromial space, which is above the rotator cuff tendon tear. A bursectomy is then preformed and the drill site is determined. A lateral port having an approximate diameter of 6 to 8 mm is made adjacent to the proximal end of the humerus 84 and the drill site.

The drill guide assembly 10 is introduced through the lateral port and loosely placed against a far lateral portion of the humeral head. The exit port locator 76 is extended from the first, retracted position, to the second, extended, position, where the second end 80 of the exit port locator 76 identifies the approximate exit port 96 location of the tunnel 94 to be formed by the bone cutting tip 56. The typical location of the exit port 96 is located adjacent to the articular margin at the medial aspect of the rotator cuff footprint. Once the desired exit port 96 location of the tunnel 94 is identified, the entry port site is determined. The fixed radius of curvature of the sleeve 28 and distal portion 16 permit the surgeon to accurately anticipate the path of the tunnel 94 formed by the bone cutting tip 56. The distal portion of the housing 12 is then held firmly against the entry port 98 site, and the exit port locator 76 may be optionally retracted back to the first position. Alternatively, the exit port locator 76 may remain in the second, or extended, position during the remainder of the process, and then be retracted once the drilling process is complete.

The flexible shaft 26 is advanced along with the bone cutting tip 56 towards the entry port 98 site. The flexible shaft 26 and/or bone cutting tip 56 causes the sleeve 28 to advance therealong. In an alternative embodiment, where the sleeve 28 is comprised of at least the first telescoping portion 40 and the second telescoping portion 42, the advancement of the bone cutting tip 56 and/or flexible shaft 26 will cause the one of the first 40 and second 42 telescoping portions to move relative to another.

The bone cutting tip 56 creates a tunnel 94 within the bone as it is advanced and rotated by the flexible shaft 26. The bone cutting tip 56 and the flexible shaft 26 travel along a path having a constant non-zero radius of curvature between the first position to the second position. The radius of curvature of the tunnel 94 formed by the bone cutting tip 56 is substantially equal to the radius of curvature of the sleeve 28 and the distal portion 16 of the housing 12. The bone cutting tip 56, flexible shaft 26, and sleeve 28 are advanced through the bone until the bone cutting tip 56 reaches the second position, and exits the bone at the predetermined exit port 96 site. The outer stop member 70 also prevents the bone cutting tip 56 from being advanced substantially beyond the exit port site.

In one embodiment, the diameter of the tunnel 94 created by the bone cutting tip 56 may be at least substantially equal to the external diameter of the distal portion 16 of the housing 12, thereby allowing a portion of the distal portion 16 of the housing 12 to enter the tunnel 94 during the drilling process if additional angular displacement of the bone cutting tip 56 is necessary to form the tunnel 94 within the bone. Specifically, the distal portion 16 of the housing 12 may be partially inserted into the tunnel 94, thereby allowing the bone cutting tip 56 to tunnel further through the bone, if necessary.

The rotation of the flexible shaft 26 and the bone cutting tip 56 may impart a rotational force on the sleeve 28, which may bind the sleeve 28 against the distal portion 16 of the housing 12 if not constrained. However, the guide 72 and channel 74 arrangement prevents the rotational relative movement of the sleeve 28, but allow the sleeve 28 to reciprocate within the distal portion 16 of the housing 12. The guide 72 and channel 74 arrangement may also function as a stop when the sleeve 28 is fully extended from the distal portion 16 of the housing 12, where the guide 72 may abut an end of the channel 74 to restrict the travel of the sleeve 28 with respect to the distal portion 16 of the housing 12.

During the drilling process, bone fragments may be accumulate within the freshly drilled tunnel 94 and may impede further drilling. Accordingly, in one embodiment, the gap between the bone cutting tip 56 and the distal end 32 of the sleeve 28 may permit these fragments to exit from the drill site and into the sleeve 28. Moreover, these fragments and other debris may also exit through the proximal portion of the sleeve via the apertures 68 formed within the stop member 60.

Upon completion of the drilling process, the drill guide assembly 10 can be removed by retracting the flexible shaft 26 and the bone cutting tip 56 from the tunnels, from the second position back to the first position. The drill guide assembly 10 may then be removed from the cannula tube. A suture may then be shuttled through the tunnel 94 and passed through the rotator cuff tendon using standard technique. The suture is tied to the rotator cuff tendon and secured to the bone. The cannulas are removed and the portals are closed with simple sutures.

Figure 12:
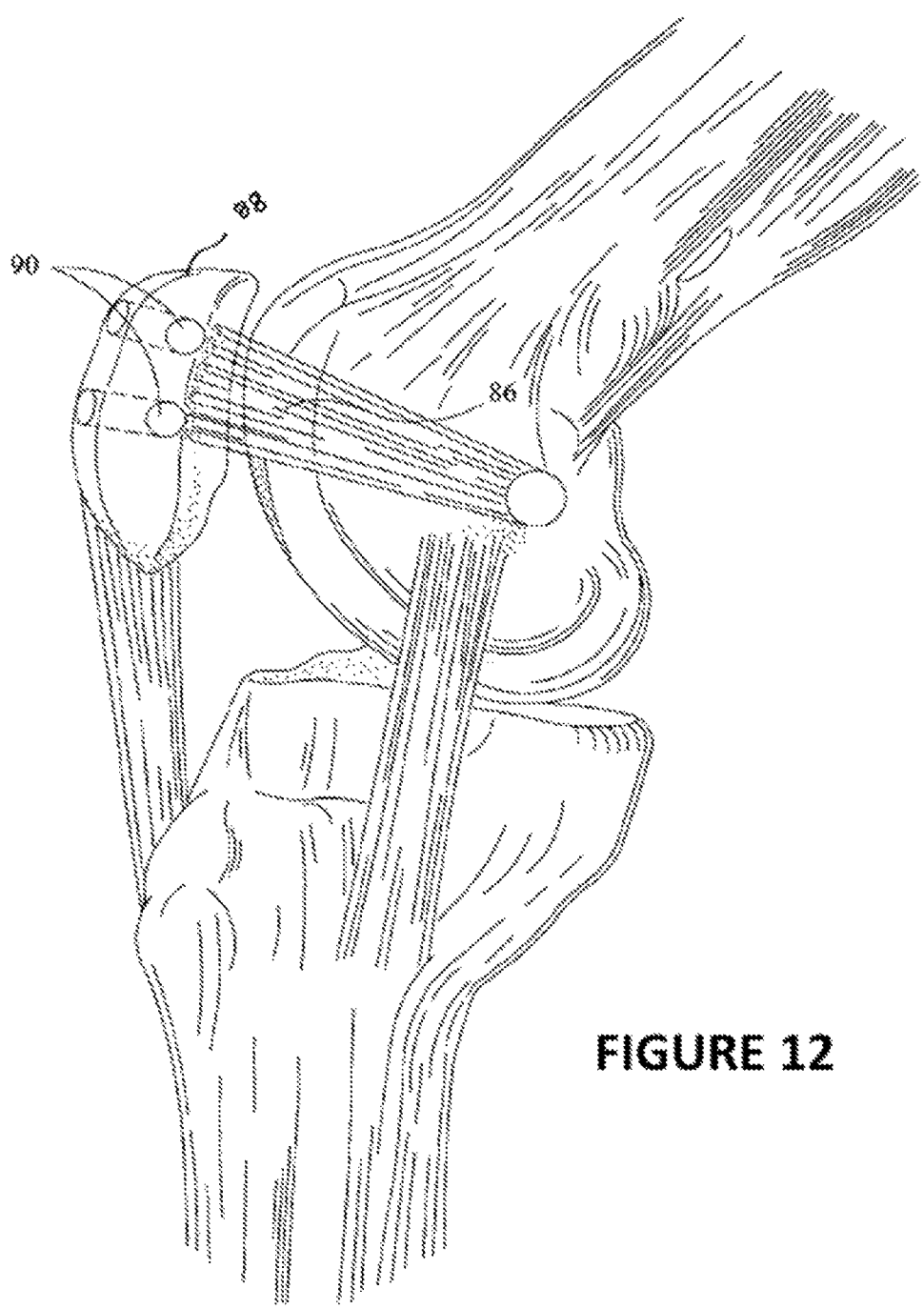
FIG. 12 is a perspective view of the medial patellofemoral ligament graft.

The drill guide assembly 10 may also be used to perform Medial Patello-Femoral Ligament (MPFL) reconstruction. During MPFL reconstruction, a medial patellofemoral ligament (MPFL) graft 86 is reattached, or resecured, to the patella 88, as shown in FIG. 12. Two tunnels 90 are created within the patella 88 which are used to secure the MPFL graft 86 to the patella 88.

To create the tunnels 90, a skin incision is made over the patella 88, and the superior, medial quadrant of the patella 88 is identified. The distal portion 16 of the drill guide assembly 10 is placed against the medial aspect of the patella 88 at a desired location of the entry port of the first tunnel. As explained above, with respect to the rotator cuff tendon repair method, the desired exit port location of the first tunnel may govern the location of the entry port of the tunnel. Accordingly, the exit port locator 76 may be extended from a first, or retracted position, to a second, or extended position, where the second end 80 of the exit port locator 76 can approximate the location of the exit port of the tunnel located on the anterior patella surface, and thus locate the entry port location of the first tunnel.

Once the entry port location is identified, the bone cutting tip 56 may be advanced in substantially the same method as described above to create the first and second tunnels 90 within the patella 88. Once the tunnels are created, an incision is made between the adductor tubercle and medial epicondyle and the desired location of femoral attachment of the MPFL graft 86 is located. An end of the MPFL graft 86 is doubled over and is secured to the femur with an interference screw. The two free tails on the other end of the MPFL graft 86 are respectfully tunneled through the medical retinaculum and are brought though the two tunnels in the patella 88. The MPFL graft 86 is tensioned appropriately and the two tails are sutured back onto themselves to secure the graft. The incision is then closed with simple sutures.

Figure 13:
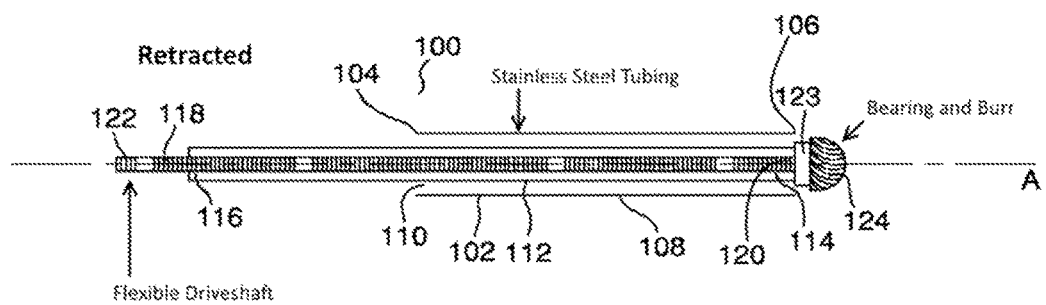
FIG. 13 is a fragmentary view of another embodiment of the drill guide assembly in a retracted position.

In an alternative embodiment described below, the orthopedic guide device is configured to create tunnels using unique superelastic properties of a material referred to commonly as "shape memory alloy." The shape memory alloy is commonly made from nickel titanium (NiTi), sometimes referred to as "SMA," also commonly known commercially as Nitinol. In this embodiment, the guide tube is shaped having a pre-formed non-zero radius of curvature. In this embodiment, and as shown in FIG. 13, a drill guide assembly 100 consists of a guide tube 102 defining an A axis. The guide tube 102 comprises a proximal portion 104, a distal portion 106, and a body portion 108 disposed between the proximal 104 and distal 106 portions. The relative lengths of the proximal 104, distal 106, and body 108 portions may vary between applications, and may be dependent on the desired maneuverability and characteristics for a particular use.

In the embodiment shown in FIG. 13, the body portion 108 has a substantially linear shape, however, the shape of the body portion 108 may vary depending on the intended use of the assembly 100. For example, the body portion 108 may also have a shape having a non-zero radius of curvature, for improved ergonomics or to reduce the amount of strain experienced by other components of the assembly 100.

As further shown in FIG. 13, a passage 110 is formed within the guide tube 102. The passage 110 generally extends from the proximal portion 104 of the guide tube 102 to the distal portion 106 of the guide tube 102, along the A axis. The passage 110 is configured to accommodate a hollow cutting tube 112 therein. The cutting tube 112 is slidably disposed within the passage 110 of the guide tube 102 and can reciprocate within the passage 110. The cutting tube 112 includes a distal end 114 adjacent to the distal portion 106 of the guide tube 102 and a proximal end 116 adjacent to the proximal portion 104 of the guide tube 102. A flexible driveshaft 118 is disposed within the cutting tube 102 such that the driveshaft 118 is coupled with the hollow cutting tube 112 but can rotate independently of the tube 112. A distal end 120 of the rotating driveshaft 118 is coupled with a bone cutting bit 124 and a proximal end 122 is configured to be attached to a driving mechanism, such as a pneumatic drill. The distal end 114 of the cutting tube 112 is coupled with the driveshaft 118 and bone cutting bit 124 such that all three components are designed to reciprocate with respect to the passage 110 together while the driveshaft 118 and bone cutting bit 124 may independently rotate with respect to the cutting tube 112. The passage 110 and/or an exterior surface of the cutting tube 112 may be coated with a lubricating compound, such as graphite or Teflon, or be made out of a material having a low coefficient of friction to reduce the frictional force generated by the relative movement between the passage 110 and the cutting tube 112.

Figure 17:
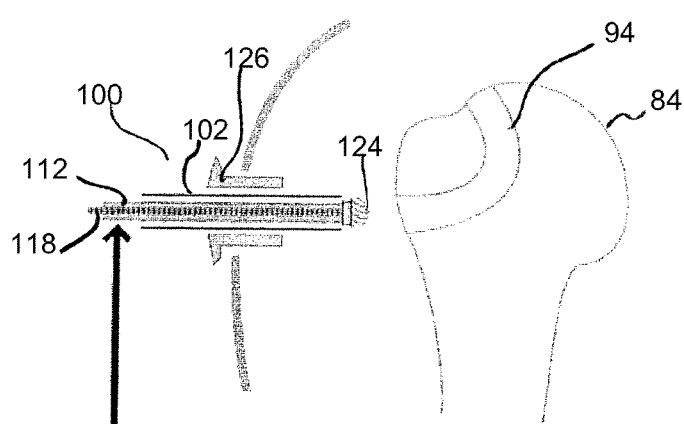
FIG. 17 is a fragmentary view of the distal end of the embodiment of the drill guide assembly shown in FIG. 13 in a retracted position adjacent to the humeral head of the patient.

The bone cutting tip 124 is disposed on the distal end 120 of the driveshaft 118. The bone cutting tip 124 is designed to create a hole, or tunnel 94 as shown in FIG. 17, having approximately the same diameter of the bone cutting tip 124 through a medium, such as bone. As shown in FIGS. 1 and 2 the bone cutting tip 124 is fixedly coupled with the distal end 120 of the driveshaft 118 via a bearing 123, with the bone cutting tip 124 being disposed adjacent to the distal end 114 of the cutting tube 112. The bone cutting tip 124 and the driveshaft 118 are configured to be able to rotate with respect to the cutting tube 112. The bone cutting tip 124 forms a hole having a diameter which is at least equal to the outer diameter cutting tube 112, to permit the cutting tube 112 to be advanced through the hole or tunnel 94 formed within the working medium. The bone cutting tip 124 may be formed out of any suitable metal alloy or plastic.

Figure 14:
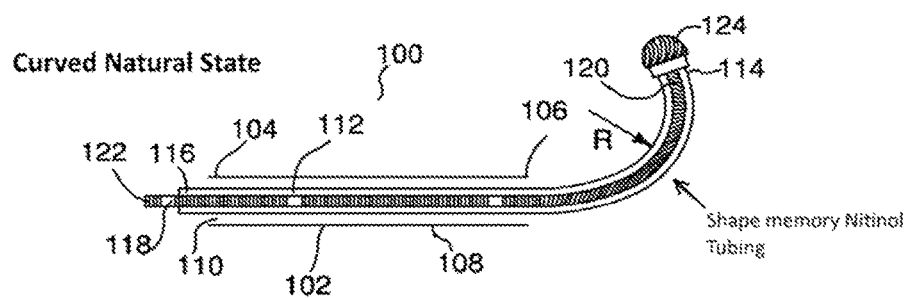
FIG. 14 is a fragmentary view of the embodiment of the drill guide assembly shown in FIG. 13 in an advanced position.
Figure 15:
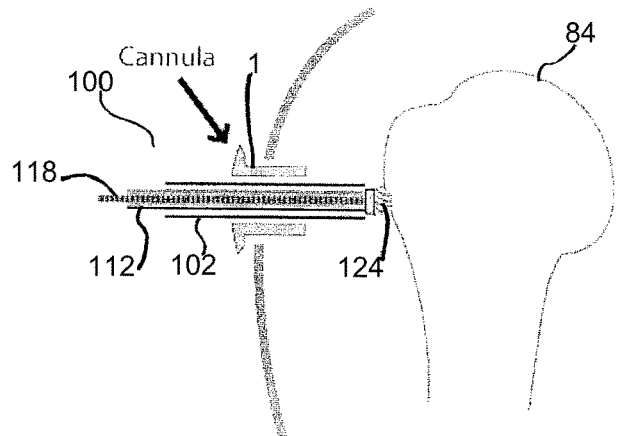
FIG. 15 is a fragmentary view of a distal end of the embodiment of the drill guide assembly shown in FIG. 13 adjacent to the humeral head of a patient.

The hollow cutting tube 112 is comprised of a shape memory alloy. A shape memory alloy enables the material to undergo a reversible phase transformation when heated above its transition temperature and is super-elastic once the transition temperature is reached and exceeded. Super-elastic infers that the material can endure greater changes in strain than standard engineering materials, such as steel or aluminum, while still returning to its initial shape when the deforming load is removed (up to 8% in shape memory alloys versus around 0.5% in steels). In this application, the super-elastic effect of the shape memory alloy is desired, therefore, the transition temperature will be designed to be well below room temperature (or whatever temperature range the product will be designed for) to ensure the super-elastic effect of the material when in use. The transition temperatures can be varied with this material by changing the composition of the primary elements of the material (i.e., nickel and titanium). The cutting tube 112 may have a preformed shape as shown in FIG. 14, with a non-zero radius of curvature. When retracted, the cutting tube 112 may be deformed from its pre-formed shape into a new shape, such as one having a large radius of curvature or that is substantially linear as seen in FIG. 13. As the cutting tube 112 is extended, the material returns to its original pre-formed shape due to the super-elastic property of the material. One such shape memory alloy is comprised of Nickel and Titanium and is commonly referred to as "Nitinol." The hollow cutting tube 112 is configured to have a preformed shape of the desired tunnel to be formed within the humeral head of the patient, such that once it is extended, the tube 112 can return to this pre-formed curved shape, which is shown in FIG. 14. If the cutting tube 112 has a small preformed radius of curvature and if it is sufficiently elastic, it will allow the cutting tube 112 to be inserted into a distal portion 106 with a larger radius of curvature. The larger radius of curvature will reduce the overall insertion profile, or width, of the distal portion 106 of the guide tube 102 and enhance the ability to maneuver the guide tube 102 during operation.

The tube 112, in this embodiment, may have a radius of curvature of 15 mm in its preformed shape and has an outer diameter of 3 mm. The radius of curvature of outer diameter of the tube 112 is not limited to these values, and may vary depending on the intended application.

For example, the preformed shape of the cutting tube 112 may have an arc-shape ranging from 0 to 360 degrees, and the fixed non-zero radius of curvature may be 0 to 50 mm. However, the exact radius of curvature desired is dependent on the bone thickness and the intended use. For example, in the embodiment shown in FIG. 14 the cutting tube 112 has a semi-circular shape with a substantially constant radius of curvature, R.

The material of the cutting tube 112 may vary depending on the properties desired for a particular procedure. Normally, metal alloys can withstand a small degree of strain (or deflection) before they start to plastically yield (i.e. become permanently deformed), on the order of 0.5%. When the cutting tube 112 is retracted inside the guide tube 102, the estimated strains created in the hollow alloy cutting tube 112 far exceed this value.

The maximum strain of the tube 112 with the aforementioned geometry constraints can be calculated, to determine if using a retractable curved tubing approach is practical. The maximum strain occurs when the tube 112 is retracted from its initial curved shape into a straight configuration.

Figure 18:
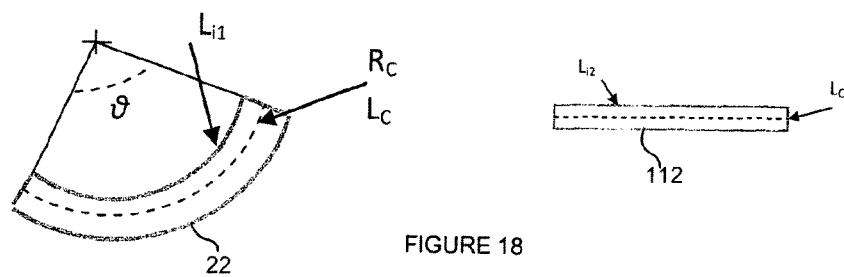
FIG. 18 is a fragmentary view of the cutting tube of the embodiment of the drill guide assembly shown in FIG. 13.

Referencing the parameters set forth in FIG. 18, strain is defined as the change in length divided by the original length of a material, as seen in equation 1 for this case, where $L_{i1}$ is the arc length of the inner edge of the material in its curved state and $L_{i2}$, is the length when it is extended.

$$\varepsilon = \frac{L_{i2} - L_{i1}}{L_{i1}} \quad [1]$$

If it is assumed that the length of the centerline ($L_c$) does not change, then for both the retracted and extended states $L_c$ is determined as seen in equation 2, where $R_c$ is the radius of curvature at the centerline and $\theta$ is the angle of the arc (in radians).

$$L_c = R_c \theta \quad [2]$$

If the tube 112 is extended perfectly straight, then Lie is also equal to $L_c$. $L_{i1}$ can be calculated with equation 3, where $\theta$ is the angle of the arc (in radians) and D is the outer diameter of the tubing.

$$L_{i1} = \left(R_c - \frac{D}{2}\right)\theta \quad [3]$$

Given the maximum allowable strain for the material, the equations can be rearranged, as seen in equation 4, to calculate the largest diameter tubing that will work with the given geometry restraints.

$$D = 2R_c\left(1 - \frac{1}{1+\varepsilon}\right) \quad [4]$$

Using a cutting tube diameter of about 2.5 mm, calculated strains equal about 8%, which is much higher than normal alloy metals permit. This would mean that normal alloys would plastically yield if they were cycled through this condition and the design approach described above would not be feasible.

However, a shape memory alloy, such as nickel titanium (NiTi), sometimes referred to as "SMA," also commonly known as Nitinol, derived from its place of discovery (Nickel Titanium Naval Ordnance Laboratory) may overcome these obstacles.

This material has at least two unique properties: 1) the ability to undergo a reversible phase transformation when heated above its transition temperature, and 2) super-elasticity. The former occurs when the material is initially below its transition temperature, and is deformed or bent. If it is then heated above its transition temperature, it will return to its pre-deformed shape (at least to a degree). Conversely, if the SMA material is already above its transition temperature, it will be super-elastic, meaning that the material can be bent or deformed (strained) to a fairly significant degree, but still return to its un-deformed shape once the applied loads are removed. While about 4%-6% recoverable strains are common, strains of up to approximately 8% ($\varepsilon = 0.08$) can be recoverable (i.e. the material can be deformed that much and still return to its original shape).

The material is composed of approximately 46 to 55% nickel by weight. The phase transition temperature can be varied significantly by making small changes in the composition of the elements. The Nitinol material can be composed such that it is super-elastic at room temperature (or whatever operating temperature is specified).

Using equation 4 (above) and an 8% strain limit and initial radius of curvature of 15 mm, the diameter of the tubing can be up to approximately 2.2 mm. Of course, the amount of strain limit and initial radius of curvature may be manipulated depending on the intended use.

Figure 19:
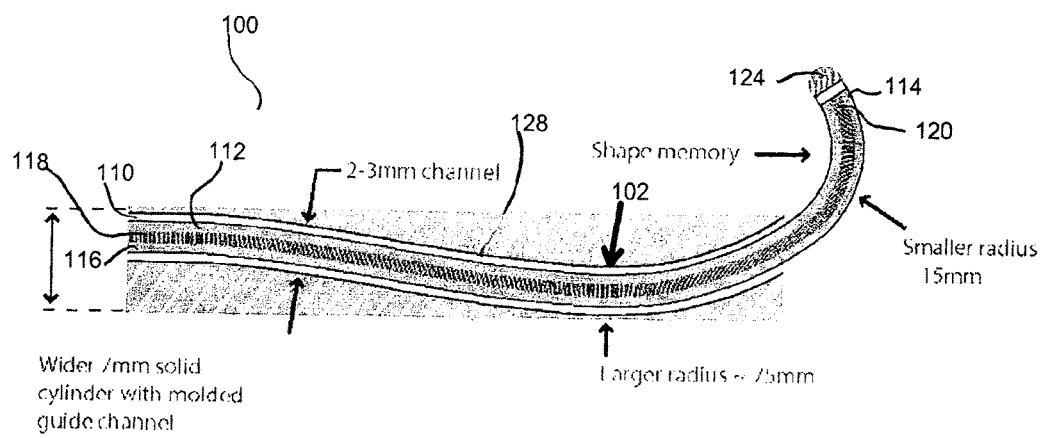
FIG. 19 is a fragmentary view of another embodiment of the drill guide assembly.
Figure 20:
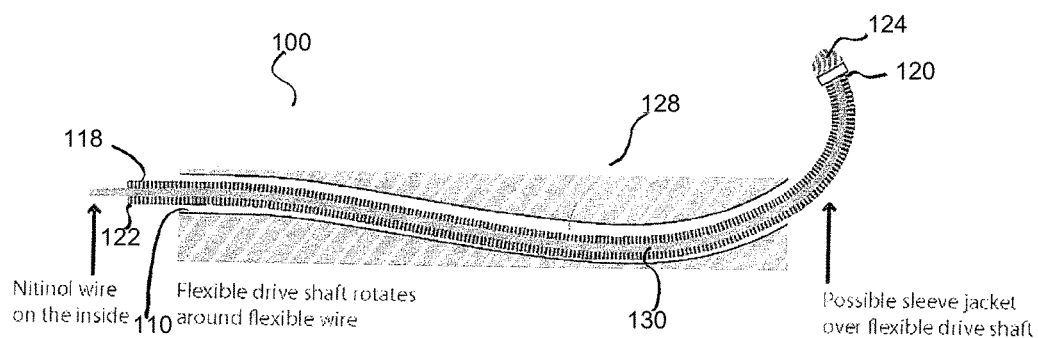
FIG. 20 is a fragmentary view of yet another embodiment of the drill guide assembly.

In an alternative embodiment, if a larger cutting tube 112 diameter is required, instead of retracting the cutting tube 112 into a substantially linear guide tube 102, the cutting tube 112 could be retracted into a larger tube 102 with a non-linear molded channel 128 having an approximate diameter from 2-3 mm with a large radius of approximately 75 mm, so the cutting tube 112 does not have to be fully straightened as shown in FIG. 19. The diameter of the channel 128 will vary depending on the application and may be greater or smaller than the 2-3 mm channel disclosed in this embodiment. The curvature of the molded channel 128 reduces the tube strain allowing the preformed diameter of the tube 112 to be increased. The total guide tube 102 diameter may be approximately 8.22 mm to fit through a standard cannula. Therefore, if the Nitinol tubing is only 2-4 mm in diameter, the diameter of the molded channel 128 may be increased to accommodate a non-linear design in order to significantly decrease the strain experienced by the cutting tube 112 prior to being extended from the guide tube 102. Alternatively, the guide tube 102 may also be modified such that it has a non-zero small radius of curvature to reduce the amount of strain experienced by the cutting tube 112 when it is in the retracted position. The radius of curvature of the guide tube 102 will not affect the ability of the guide tube 102 to be inserted through a standard arthroscopic portal.

In another embodiment shown in FIG. 110, the cutting tube 112 may be replaced with a wire 130 made out of a memory shape alloy, such as Nitinol, with the driveshaft 118 encircling the wire 130. In this embodiment, the driveshaft 118 may be formed of a spring coil that would be hollow inside. The wire 130, when extended, would cause the driveshaft 118 to take on the curved preformed shape of the wire 130. The wire 130 would have less strain due to its smaller diameter.

Figure 21:
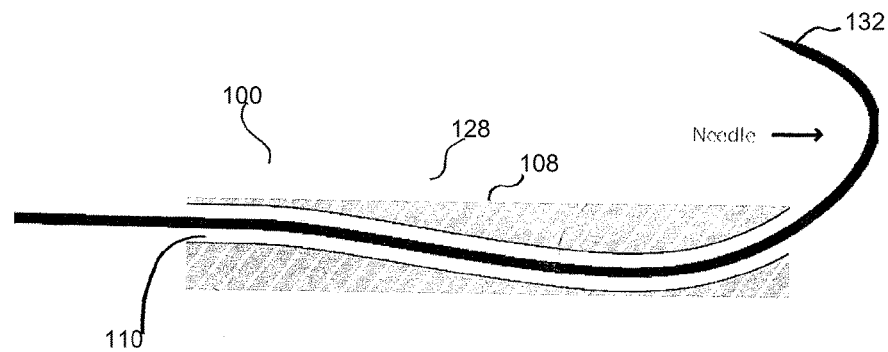
FIG. 21 is a fragmentary view of yet another embodiment of the drill guide assembly.

In yet another embodiment, as shown in FIG. 21, the bone cutting bit 124 at the distal end of the wire 130 may be replaced with a piercing needle 132 to penetrate the bone medium. A pneumatic impact driver, such as an impact gun, drives the wire 130 to create a tunnel within the bone medium. The impact of the piercing needle 132 removes fragments of the bone in order to create the curved tunnel 94. There is minimal relative rotation between the wire 130 and the channel 128 order to create the tunnel. Therefore, a driveshaft to rotate the wire 130 may not be necessary in this particular embodiment. Also, the channel 128 may also have a non-zero radius of curvature along its length to reduce the amount of strain on the wire 130.

During the surgical procedure, a surgeon investigates the glenohumeral joint by creating a posterior arthroscopic portal. An arthroscope (not shown) is introduced into the glenohumeral joint to an area proximate to the damaged rotator cuff tendon. An anterior portal having a diameter of 6 to 8 mm is made and an anterior cannula is inserted into the portal to perform a standard glenohumeral arthroscopy procedure. Once the damaged area is identified, the arthroscope and anterior cannula are repositioned to the subacromial space, which is above the rotator cuff tendon tear. A bursectomy is then preformed and the drill site is determined. A lateral port having an approximate diameter of 6 to 8 mm is made adjacent to the proximal end of the humerus 84 and the drill site.

Figure 16:
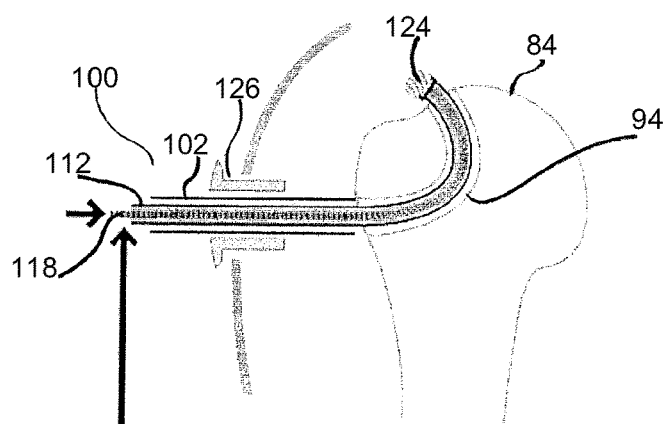
FIG. 16 is a fragmentary view of the distal end of the embodiment of the drill guide assembly shown in FIG. 13 advanced through the humeral head of the patient.

During the surgical procedure, the lateral port is created in substantially the same way as described above. Then, the drill guide assembly 100 is introduced through the lateral port and loosely placed against a far lateral portion of the humeral head 84 through a cannula 126. During an arthroscopic procedure, the cutting tube 112 and flexible driveshaft 118 are retracted inside the guide tube 102 and located adjacent to the intended drill site as shown in FIG. 13. In this embodiment, the cutting tube 112 is above its transition temperature and therefore is super-elastic. However, it is contemplated that the phase change may occur during the procedure so as to permit portions of the cutting tube 112 to transition to being super-elastic once extended from the guide tube 102. However, in this embodiment, the cutting tube 112 is above the transition temperature and therefore in its super-elastic phase prior to placing the assembly 100 adjacent to the humeral head. After inserting this assembly 100 into the cannula 126, the surgeon would locate the drill tool at the desired location on the humeral head 84 and then actuate the tool. Upon actuation, the cutting tube 112 would slowly be extended out of the guide tube 102 while the flexible driveshaft 118 and cutting bit 124 rotate. The flexible driveshaft 118 and cutting bit 124 would extend along with the cutting tube 112, with the cutting bit 124 creating a tunnel 94 in the bone as it moves forward. As extended beyond the guide tube 102, the shape of the hollow cutting tube 112 will be permitted to take on its initially pre-formed shape, as shown in FIG. 14. As the cutting tube 112 continues to extend, a curved tunnel 94 would be created in the humeral head 84 as shown in FIG. 16 having a shape similar to that of the pre-formed shape of the hollow cutting tube 112.

Upon completion of the drilling process, the drill guide assembly 100 can be removed by retracting the cutting tube 112, driveshaft 118, and the bone cutting tip 124 from the tunnel 94 as shown in FIG. 17. If the preformed shape of the cutting tube 112 inhibits it from being retracted back into the guide tube 102, the drill guide assembly 100 may be removed form the cannula tube 126 without retracting the cutting tube 112 into the guide tube 102.

Once the drill guide assembly 100 is removed from the cannula tube 126, a suture may then be shuttled through the tunnel 94 and passed through the rotator cuff tendon using standard technique. The suture is tied to the rotator cuff tendon and secured to the bone. The cannulas are removed and the portals are closed with simple sutures.

It can be appreciated that the drill guide assembly 100 may also be used to perform other medical procedures requiring a substantially curved tunnel. For example, the assembly 100 can be used to perform Medial Patello-Femoral Ligament (MPFL) reconstruction. During MPFL reconstruction, a medial patellofemoral ligament (MPFL) graft is reattached, or resecured, to the patella. Two tunnels are created within the patella which are used to secure the MPFL graft to the patella.

The invention claimed is:

1. A guide assembly for forming a tunnel within a bone, the guide assembly comprising:
a housing having a substantially linear proximal portion, including an elongate handle, and a curved distal portion having a distal end, wherein the curved distal portion has a radius of curvature;
a passage extending through the proximal portion to the distal portion and that terminates at the distal end;
a flexible shaft having a distal end comprising a piercing member, wherein the flexible shaft is configured to be disposed in and to move relative to the passage;
a sleeve configured to be disposed in and to move relative to the passage, wherein the flexible shaft is configured to be slidingly disposed within the sleeve;
where in a first position at least a portion of the sleeve and the piercing member are disposed within the passage of the distal portion of the housing, and the distal end of the housing is configured to abut against an external surface of the bone to maintain the first position; and
where in a second position the sleeve and at least a portion of the piercing member extend from the distal portion of the housing, where the sleeve and the piercing member maintain the radius of curvature of the distal portion as the sleeve and the piercing member extend from the distal portion.

2. The guide assembly of claim 1, wherein the piercing member is a drill bit.

3. The guide assembly of claim 1, wherein the sleeve is rotationally fixed about a longitudinal axis that extends along a length of the housing.

4. The guide assembly of claim 1, where in the second position at least a portion of the sleeve extends from the housing.

5. The guide assembly of claim 4, wherein the at least a portion of the sleeve has a shape that is substantially the same as the distal portion of the housing.

6. The guide assembly of claim 4, wherein a distal end of the sleeve is configured to abut against the external surface of the bone.

7. The guide assembly of claim 4, wherein the at least a portion of the sleeve is configured to extend into the bone.

8. A guide assembly for forming a tunnel within a bone, the guide assembly comprising:
a housing having a substantially linear proximal portion, including a handle, that transitions to a curved distal portion having a distal end, the curved distal portion having a radius of curvature;
a passage formed within the housing, wherein the passage is substantially linear along a length of the substantially linear proximal portion of the housing, and wherein the passage is curved within the curved distal portion of the housing and extends through the distal portion and terminates at the distal end;
a piercing member configured to be disposed in the passage at the distal portion of the housing and to move relative to the passage such that it moves away from the proximal portion and extends from the distal end of the housing while it maintains the radius of curvature; and
a sleeve configured to be disposed in and to move relative to the passage, wherein the piercing member is configured to be slidingly disposed within the sleeve.

9. The guide assembly of claim 8, wherein an outer diameter of the piercing member is between 1 mm to 15 mm.

10. The guide assembly of claim 8, wherein the piercing member is not rotationally fixed about a longitudinal axis that extends along a length of the housing.

11. A guide assembly for forming a tunnel within a bone, the guide assembly comprising:
a housing having a substantially linear proximal portion including an elongate handle and a curved distal portion having a distal end, wherein the curved distal portion has a radius of curvature;
a passage formed within the housing, wherein the passage is substantially linear along a length of the substantially linear proximal portion of the housing, and wherein the passage is curved within the curved distal portion of the housing and terminates at the distal end;
a flexible shaft having a distal end comprising a piercing member, wherein the flexible shaft is configured to be disposed in and to move relative to the passage; and
a sleeve configured to be disposed in and to move relative to the passage, wherein the piercing member is configured to be slidingly disposed within the sleeve;
where in a first position at least a portion of the sleeve and the piercing member are disposed within the passage of the distal portion of the housing, and the distal end of the housing is configured to abut against an external surface of the bone to maintain the first position; and
where in a second position at least a portion of the piercing member is moved in a direction away from the proximal portion and extends from the distal end of the housing into the bone while maintaining the radius of curvature, such that the piercing member forms the tunnel within the bone, and where the distal end of the housing is configured to abut against the external surface of the bone.

12. The guide assembly claim 11, wherein the sleeve is rotationally fixed about a longitudinal axis that extends along a length of the housing.

13. The guide assembly of claim 11, where in the second position at least a portion of the sleeve extends from the housing.

14. The guide assembly of claim 13, wherein a distal end of the sleeve is configured to abut against the external surface of the bone.

15. The guide assembly of claim 13, wherein the at least a portion of the sleeve is configured to extend into the bone.

16. A guide assembly for forming a tunnel within a bone, the guide assembly comprising:
a housing having a substantially linear proximal portion including an elongate handle and having a longitudinal axis, and a distal portion having a distal opening, wherein the distal opening forms a plane that is substantially perpendicular to the longitudinal axis of the proximal portion of the housing;
a passage extending through the proximal portion to the distal portion and terminating at the distal opening;
a flexible shaft having a distal end comprising a piercing member, wherein the flexible shaft is configured to be disposed in and to move relative to the passage and extend from the distal opening of the housing;
a sleeve configured to be disposed in and to move relative to the passage, wherein the flexible shaft is configured to be slidingly disposed within the sleeve;
where in a first position at least a portion of the sleeve and the piercing member are disposed within the passage of the distal portion of the housing, and a distal end of the housing is configured to abut against an external surface of the bone to maintain the first position; and
where in a second position at least a portion of the piercing member is moved in a direction away from the proximal portion and extends from the distal opening of the housing into the bone, such that the piercing member forms the tunnel within the bone, and where the distal end of the housing is configured to abut against the external surface of the bone.

\* \* \* \* \*